United States Patent
Geng et al.

(10) Patent No.: US 12,269,838 B2
(45) Date of Patent: *Apr. 8, 2025

(54) COMPOSITION OF MANNURONIC DIACID

(71) Applicants: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

(72) Inventors: Meiyu Geng, Shanghai (CN); Jian Ding, Shanghai (CN); Zhenqing Zhang, Suzhou (CN); Zhongping Xiao, Shanghai (CN); Xiaoguang Du, Shanghai (CN); Xianliang Xin, Shanghai (CN)

(73) Assignees: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 243 days.

This patent is subject to a terminal disclaimer.

(21) Appl. No.: 17/860,468

(22) Filed: Jul. 8, 2022

(65) Prior Publication Data
US 2022/0356202 A1 Nov. 10, 2022

Related U.S. Application Data

(63) Continuation of application No. 16/474,928, filed as application No. PCT/CN2017/118843 on Dec. 27, 2017, now Pat. No. 11,384,111.

(30) Foreign Application Priority Data

Dec. 30, 2016 (WO) ................ PCT/CN2016/113879

(51) Int. Cl.
*C07H 15/04* (2006.01)
*A61K 31/7032* (2006.01)
*A61K 31/715* (2006.01)
*A61P 25/28* (2006.01)
*C08B 37/00* (2006.01)

(52) U.S. Cl.
CPC ......... *C07H 15/04* (2013.01); *A61K 31/7032* (2013.01); *A61K 31/715* (2013.01); *A61P 25/28* (2018.01); *C08B 37/0084* (2013.01)

(58) Field of Classification Search
CPC ............ C08B 37/0084; A61K 31/7032; A61K 31/715
See application file for complete search history.

(56) References Cited

U.S. PATENT DOCUMENTS

| 8,835,403 B2 | 9/2014 | Geng et al. |
| 11,384,111 B2 | 7/2022 | Geng et al. |
| 2019/0255092 A1 | 8/2019 | Geng et al. |

FOREIGN PATENT DOCUMENTS

| CN | 100508985 C | 7/2009 |
| CN | 106344592 A | 1/2017 |
| CN | 106344593 A | 1/2017 |
| CN | 106344594 A | 1/2017 |
| CN | 106344595 A | 1/2017 |
| CN | 106349298 A | 1/2017 |
| EP | 1736160 A1 | 12/2006 |
| JP | 2007-530718 A | 11/2007 |
| JP | 2016-108474 A | 6/2016 |
| WO | 2005/089776 A1 | 9/2005 |

OTHER PUBLICATIONS

Marcq, Olivier et al., Carbohydrate Research, "Origin and significance of the production of carbon dioxide during the ozonization of 13C-labeled D-glucose at different pH values", 2001, vol. 333, pp. 233-240 (Year: 2001).*
Marcq, Olivier et al., Carbohydrate Research, "Reaction pathways of glucose oxidation by ozone under acidic conditions", 2009, vol. 344, pp. 1303-1310 (Year: 2009).*
Thaburet, Jean-Francois et al., Carbohydrate Research, "TEMPO-mediated oxidation of maltodextrins and D-glucose: effect of pH on the selectivity and sequestering ability of the resulting polycarboxylates", 2001, vol. 330, pp. 21-29 (Year: 2001).*
Azm et al., Effects of M2000 (D-Mannuronic Acid) on Learning, Memory Retrieval, and Associated Determinants in a Rat Model of Alzheimer's Disease. Am J Alzheimers Dis Other Demen. Feb. 2017;32(1):12-21.
Hu et al., Acidic oligosaccharide sugar chain, a marine-derived acidic oligosaccharide, inhibits the cytotoxicity and aggregation of amyloid beta protein. J Pharmacol Sci. Jun. 2004;95(2):248-55.

(Continued)

*Primary Examiner* — Bahar Craigo
(74) *Attorney, Agent, or Firm* — McCarter & English, LLP; Wei Song

(57) ABSTRACT

The present invention relates to a mannuronic diacid oligosaccharide composition, comprising a mannuronic diacid of Formula (III) or a pharmaceutically acceptable salt thereof, wherein n is an integer from 1 to 9, m is 0, 1 or 2, and m' is 0 or 1, and wherein the total weight of mannuronic diacids wherein n=1-5 is 80-95% of the total weight of the composition, and the ratio of the total weight of mannuronic diacids wherein n=1-3 to the total weight of mannuronic diacids wherein n=4-7 is between 1.0 and 3.5.

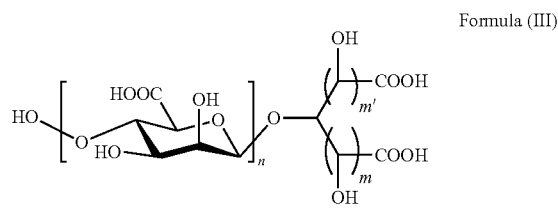

Formula (III)

17 Claims, 9 Drawing Sheets

(56) References Cited

OTHER PUBLICATIONS

Jiang et al., Synthesis and bioassay of beta-(1,4)-D-mannans as potential agents against Alzheimer's disease. Acta Pharmacol Sin. Dec. 2013;34(12):1585-91.
Liu et al., Identificaiton of AOSC-binding proteins in neurons. Chinese Journal of Oceanology and Limnology. 2008;26(4):394-399.
Xu et al., Characterization and Immunological Evaluation of Low-Molecular-Weight Alginate Derivatives. Current Topics in Medicinal Chemistry. 2016;16:874-887.
Yang et al., Preparation and characterization of oligomannuronates from alginate degraded by hydrogen peroxide. Carbohydrate Polymers. 2004;58:115-121.
Indian Office Action for Application No. 201947027009, dated Mar. 6, 2020, 5 pages.
International Search Report and Written Opinion for Application No. PCT/CN2017/118843, dated Mar. 29, 2018, 11 pages.
Japanese Office Action for Application No. 2019-556407, dated Jul. 2, 2021, 6 pages.

\* cited by examiner

COMPOSITION OF MANNURONIC DIACID

CROSS-REFERENCE TO RELATED APPLICATIONS

This application is Continuation of U.S. application Ser. No. 16/474,928, filed on Jun. 28, 2019, which is a U.S. national stage filing, under 35 U.S.C. § 371(c), of International Application No. PCT/CN2017/118843, filed on Dec. 27, 2017, which claims priority to International Application No. PCT/CN2016/113879, filed on Dec. 30, 2016. The entire contents of each of the aforementioned applications are incorporated herein by reference.

TECHNICAL FIELD

The present invention relates to an optimal composition of mannuronic diacids obtained by a biological activity screening method, which uses an animal model of senile dementia to evaluate the effects of different polymerization degrees and proportions of mannuronic diacids on the biological activity thereof. The composition with the best biological activity was finally screened and the desired target substance was prepared by ultrafiltration membrane separation.

BACKGROUND OF THE INVENTION

Mannuronic diacids have been paid extensive attention due to their potential medicinal values. Mannuronic diacids are usually prepared by a multi-step method using alginic acid as a raw material.

The polysaccharide molecule of the raw material, alginic acid, comprises an M segment formed of D-mannuronic acids linked by β-1,4-glycosidic bonds, a G segment formed of L-guluronic acids linked by α-1,4-glycosidic bonds, and a hybrid MG segment formed of the two saccharides. The structural formulae of mannuronic acid and guluronic acid are shown in the following Formula (I):

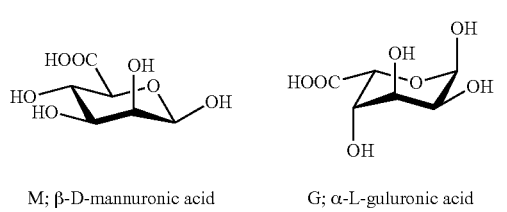

M; β-D-mannuronic acid      G; α-L-guluronic acid

The M and G segments can be separated from the raw material, alginic acid. A common method can be simply described below: alginic acid is preliminarily degraded to give a polysaccharide mixture of polymannuronic acid and polyguluronic acid; the polysaccharide mixture is subjected to acidic precipitation to remove the polyguluronic acid therein; and further refinement is conducted to obtain a homopolymannuronic acid having a purity of 90% or more (hereinafter also referred to as "M-segment intermediate"). See, e.g., the methods disclosed in Chinese Patent Application No. 98806637.8 and CN02823707.2.

Oligomannuronic acid can be prepared as follows: the M-segment intermediate obtained above is subjected to further acidolysis by heating under an acidic condition to obtain a small fragment mannuronic acid polymer having a desired range of molecular weight. In addition, the degradation efficiency can be improved by an oxidative degradation method; meanwhile, the reducing end can be oxidized to a ring-opened saccharic acid, see Chinese Patent Application No. 200580009396.5 (Patent literature 1) filed by Meiyu Geng, et al. and U.S. Pat. No. 8,835,403 B2 (Patent literature 2). For convenience, Patent literatures 1 and 2 are hereinafter collectively referred to as prior patents, which are incorporated herein by reference in their entirety.

The reaction process of mannuronic diacid disclosed in prior patents can be represented by the following reaction equation (II), that is, the aldehyde group at position C1 of mannuronic acid at the reducing end of oligomannuronic acid polysaccharide is oxidized to a carboxyl group.

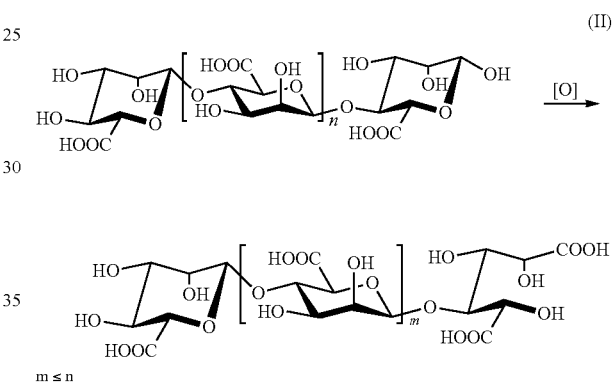

In the above oxidative conversion process, a commonly used oxidant is an alkaline copper sulfate solution, i.e., Fehling's reagent. Prior patents just adopt this oxidation method. Specifically, under an alkaline condition, the reaction substrate polymannuronic acid, i.e., the above M-segment intermediate, is added to a copper sulfate solution and reacted in a boiling water bath for 15 minutes to 2 hours. The method uses $Cu^{2+}$ ions as an oxidizing agent to oxidize the aldehyde group, and a brick-red cuprous oxide precipitate is generated in the reaction. This reaction is often used to identify a reduced sugar.

Prior patents disclose that oligomannaric acids have effects against Alzheimer's disease (AD) and Diabetes Mellitus. The pathogenesis of Alzheimer's disease and type 2 diabetes is closely related to amyloids (β-amyloid and amylin). Amyloids can aggregate to form protein oligomers, and can further aggregate to form fibers. These protein aggregates are cytotoxic, can induce an oxidation reaction in cells to damage mitochondria, and can trigger a cascade reaction such as inflammatory response, causing damage to a large number of neurons and beta cells, and ultimately leading to onset of Alzheimer's disease and type 2 diabetes. Oligomannaric acids target amyloids and antagonize the cascade reactions induced by the amyloids, and therefore have the effects of preventing and treating Alzheimer's disease and type 2 diabetes.

SUMMARY OF THE INVENTION

A first aspect of the present invention relates to a mannuronic diacid oligosaccharide composition, comprising a mannuronic diacid of Formula (III) or a pharmaceutically acceptable salt thereof:

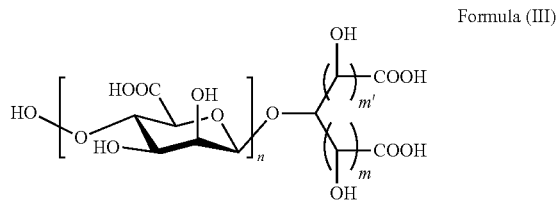

Formula (III)

wherein n is an integer from 1 to 9, m is 0, 1 or 2, and m' is 0 or 1,
and wherein,
the total weight of mannuronic diacids wherein n=1-5 is 80-95% of the total weight of the composition, and
the ratio of the total weight of mannuronic diacids wherein n=1-3 to the total weight of mannuronic diacids wherein n=4-7 is between 1.0 and 3.5.

Another aspect of the present invention provides a pharmaceutical composition or a health care product comprising the mannuronic diacid oligosaccharide composition of the present invention and, if necessary, a suitable carrier.

A further aspect of the present invention provides a method for treating a patient with senile dementia, comprising administering an effective amount of the mannuronic diacid oligosaccharide composition of the present invention to a patient in need thereof.

The mannuronic diacid oligosaccharide composition of the present invention is prepared by a method different from that of the prior art. This method of preparation has the advantages of a simple reaction, a high content of active ingredient, and no residual reaction reagents. It has been experimentally demonstrated that the mannuronic diacid oligosaccharide composition of the present invention can inhibit cell damage, protect nerve cells, and increase cell survival rate. In an animal model, the mannuronic diacid oligosaccharide composition of the present invention can significantly improve the learning and cognitive functions of dementia rats. The mannuronic diacid oligosaccharide composition of the present invention has potential effects of preventing and treating Alzheimer's disease.

DETAILED DESCRIPTION OF THE INVENTION

Figure 1:
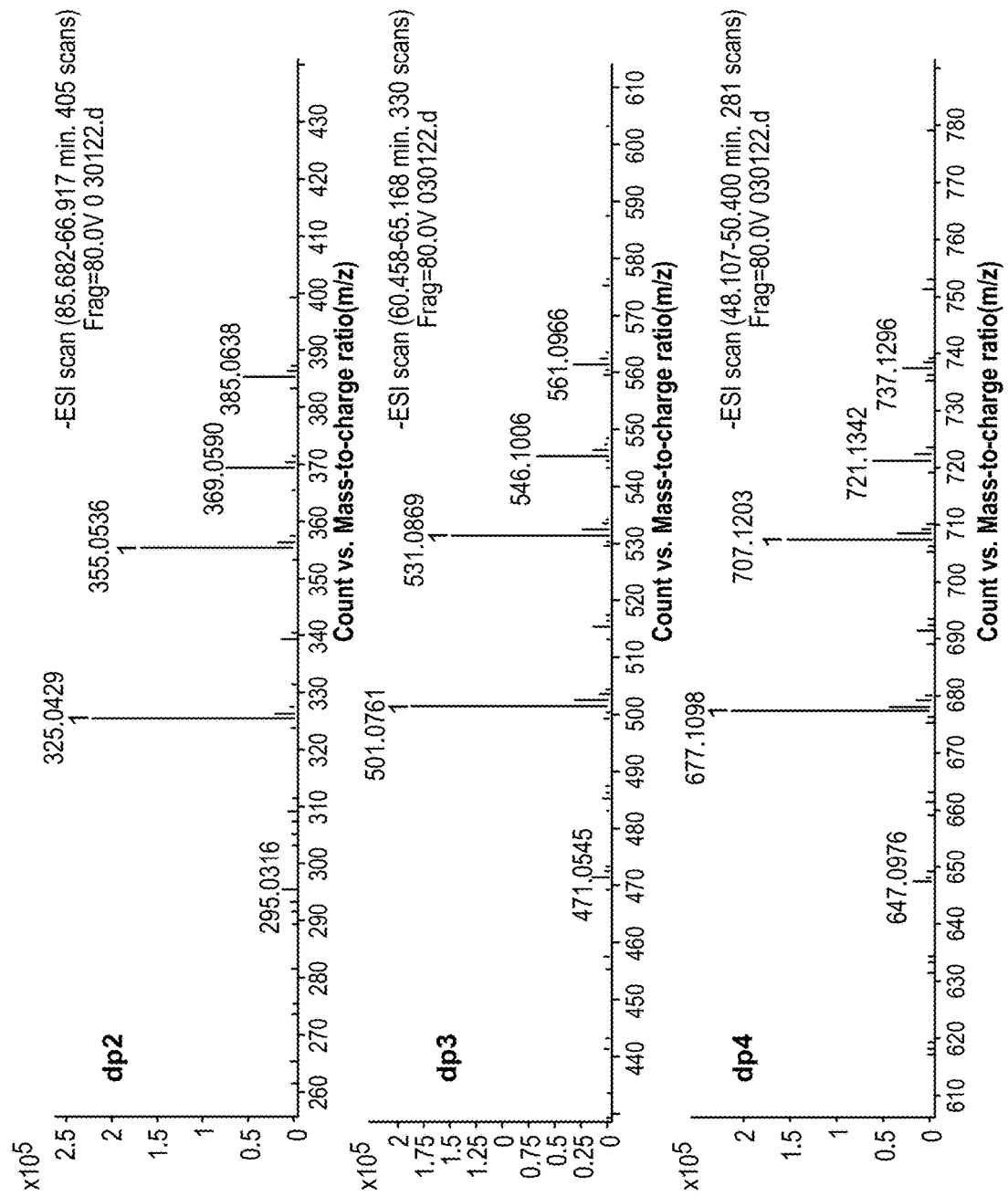
FIG. 1 shows mass spectra of disaccharide, trisaccharide and tetrasaccharide in product A.

Various aspects of the present invention will be described in detail below. However, the present invention is not limited to these specific embodiments. A person skilled in the art can make some modifications and adjustments to the present invention in light of the substantial disclosure below, and such modifications are also encompassed in the scope of the present invention.

Mannuronic Diacid Oligosaccharide Composition

A first aspect of the present invention relates to a mannuronic diacid oligosaccharide composition, comprising a mannuronic diacid of Formula (III) or a pharmaceutically acceptable salt thereof:

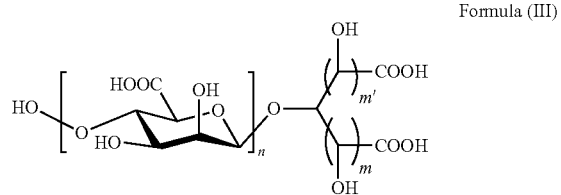

Formula (III)

wherein n is an integer from 1 to 9, m is 0, 1 or 2, and m' is 0 or 1,
and wherein,
the total weight of mannuronic diacids wherein n=1-5 is 80-95% of the total weight of the composition, and the ratio of the total weight of mannuronic diacids wherein n=1-3 to the total weight of mannuronic diacids wherein n=4-7 is between 1.0 and 3.5.

The mannuronic diacid oligosaccharide composition of the present invention is a mixture of mannuronic diacids with different polymerization degrees, and the main components thereof are mannuronic diacid oligosaccharides with a polymerization degree of 2 to 10. According to the prior applications, the most active saccharides in mannuronic diacids are from pentasaccharide to octasaccharide, in particular hexasaccharide. However, unlike the known prior art, the inventors have found that addition of less active disaccharide to tetrasaccharide to the most active pentasaccharide to octasaccharide yields a biological activity better than that of pentasaccharide to octasaccharide, under the condition of diluting the concentrations of the highly active saccharides.

According to a preferred embodiment, in the mannuronic diacid oligosaccharide composition of the present invention, the total weight of mannuronic diacids wherein m+m'=1 or 2 is not less than 50% or more, preferably 60-90%, more preferably 70-90% of the total weight of the composition. In particular, in the mannuronic diacid oligosaccharide composition of the present invention, the total weight of mannuronic diacids wherein m+m'=1 is not less than 10%, preferably 30-40% of the total weight of the composition. In another preferred embodiment, in the mannuronic diacid oligosaccharide composition of the present invention, the total weight of mannuronic diacids wherein m+m'=2 is not less than 10%, preferably 30-50% of the total weight of the composition.

According to a preferred embodiment, in the mannuronic diacid oligosaccharide composition of the present invention, the total weight of the mannuronic diacid oligosaccharides wherein n=1-5 is 80-95% of the total weight of the composition.

According to a preferred embodiment, in the mannuronic diacid oligosaccharide composition of the present invention, the total weight of the mannuronic diacid oligosaccharides wherein n=1-3 is 20-70% of the total weight of the composition.

According to a preferred embodiment, in the mannuronic diacid oligosaccharide composition of the present invention, the ratio of the total weight of the mannuronic diacids wherein n=1-3 to the total weight of the mannuronic diacid oligosaccharides wherein n=4-7 is between 1.0 and 3.5, preferably between 1.0 and 3.0.

According to a preferred embodiment, in the mannuronic diacid oligosaccharide composition of the present invention, the weight percentages of mannosonic diacid oligosaccharides with difference polymerization degrees in the composition are: 5-25% disaccharide, 15-30% trisaccharide, 15-25% tetrasaccharide, 10-25% pentasaccharide, 5-15% hexasaccharide, 3-10% heptasaccharide, 2-5% octasaccharide, 1-5% nonasaccharide, and 1-5% decasaccharide. In particular, the weight percentages of the oligosaccharides in the composition are: 10-20% disaccharide, 18-30% trisaccharide, 15-25% tetrasaccharide, 15-20% pentasaccharide, 5-10% hexasaccharide, 3-5% heptasaccharide, 2-3% octasaccharide, 1-3% nonasaccharide, and 1-3% decasaccharide.

In the mannuronic diacid oligosaccharide composition of the present invention, the pharmaceutically acceptable salt is a sodium salt or a potassium salt.

Method for Preparing a Mannuronic Diacid Oligosaccharide Composition

The process for preparing mannuronic diacid according to the present invention is summarized as follows.

The M-segment intermediate as described above is oxidatively degraded on the sugar chain in the presence of an oxidizing agent to give oxidized oligosaccharides with different polymerization degrees. The oxidized oligosaccharides are characterized in that the mannuronic acids at the reducing end of the oligosaccharides have been oxidized to saccharic acids having 3-6 carbon atoms.

The oxidizing agent which is particularly advantageous to the reaction of the present invention is ozone. During the reaction, the oxidative degradation reaction of the sugar chain occurs when ozone is introduced into a solution containing the M-segment intermediate. The temperature at which the oxidative degradation step is carried out is preferably 0-70° C., more preferably 10-45° C. The pH at which the oxidative degradation step as described above is carried out is 3-13, preferably 4-10, more preferably 6-8.

The oxidative degradation reaction using ozone in the present invention and the oxidative degradation using alkaline copper sulfate (prior patents) or acid hydrolysis in the presence of hydrogen peroxide and sodium hypochlorite (Chinese Patent Application No. 01107952.5) in the prior art all cause degradation of the sugar chain, but the structures at reducing ends of sugar chains of the degradation products are different: the oxidative degradation product obtained in the present invention, mannuronic diacid, has a diacid structure having 3-6 carbon atoms at the reducing end. Additionally, the process used in the oxidative degradation step of the present invention also offers other advantages: 1) the reaction condition is mild, and no special reaction condition is required; 2) the ozone used can be prepared in situ, and thus the transportation pressure is reduced in industrial production; and 3) after the reaction, the ozone is automatically decomposed into oxygen, and thus there is no harm caused by residual reaction reagents or environmental pollution. The reaction process is shown in the following equation (IV):

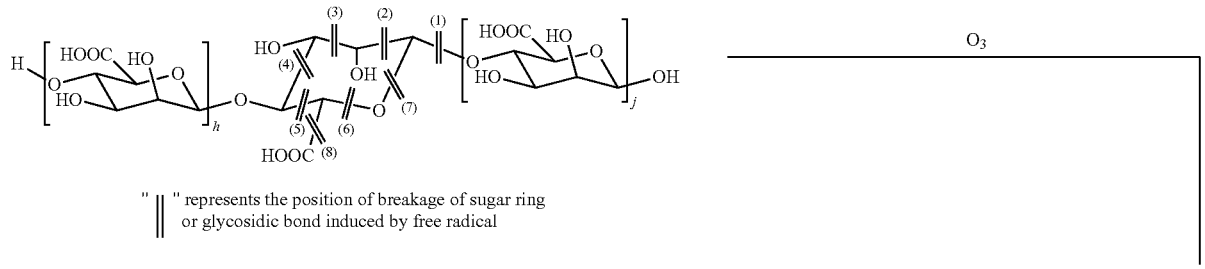

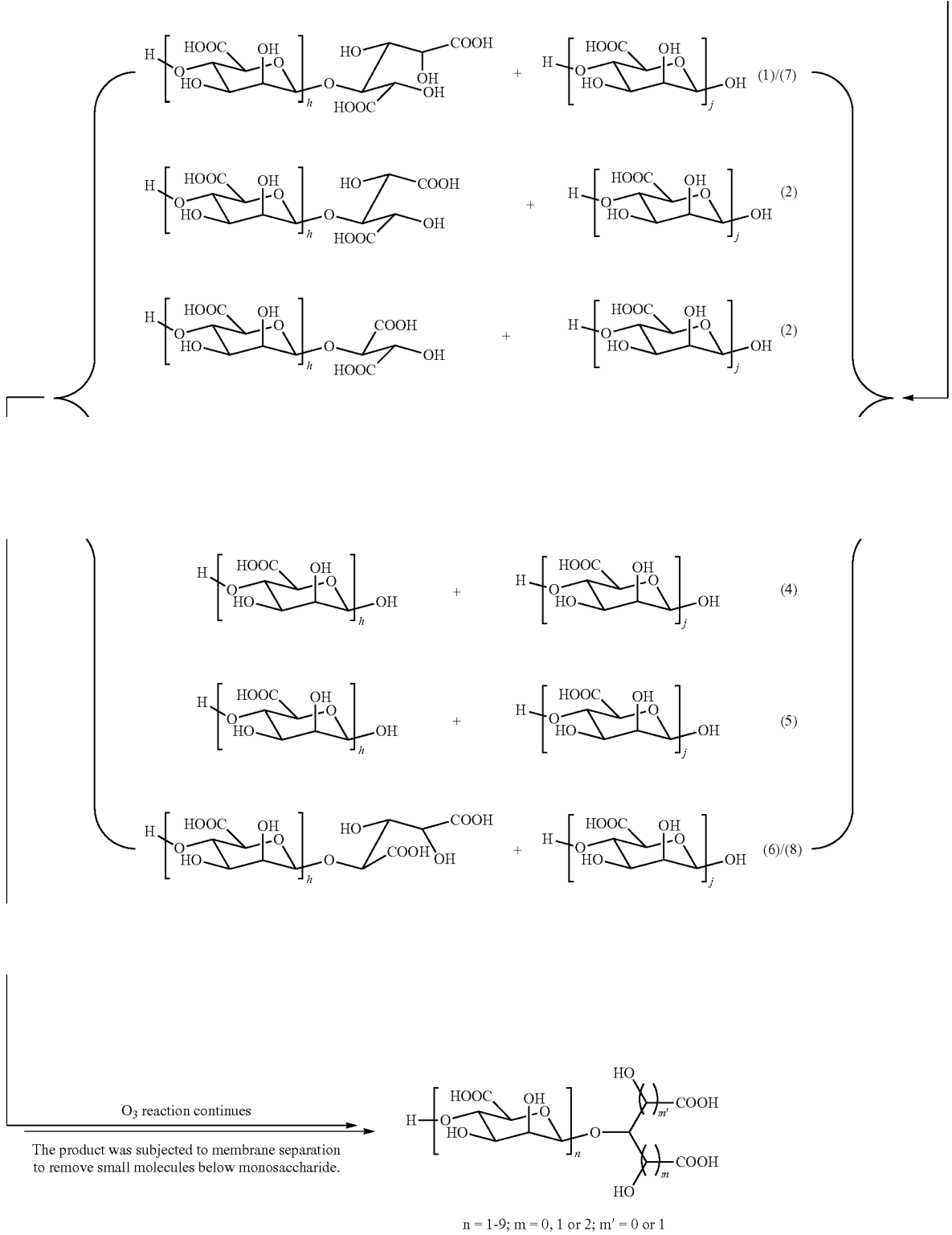

n = 1-9; m = 0, 1 or 2; m' = 0 or 1

In the schematic diagram of the above reaction equation (IV) and the compound of Formula (III), an oligosaccharide wherein m=2 and m'=1 is a saccharic acid comprising 6 carbon atoms;

an oligosaccharide wherein m=1 and m'=1 or (m=2 and m'=0) is a saccharic acid comprising 5 carbon atoms;

an oligosaccharide wherein m=1 and m'=0 or (m=0 and m'=1) is a saccharic acid comprising 4 carbon atoms; and an oligosaccharide wherein m=0 and m'=0 is a saccharic acid comprising 3 carbon atoms.

The above reaction product is desalted by membrane separation to obtain product A, as determined by LC-MS structure verification and oligosaccharide proportion measurement. The oligosaccharide proportion is determined by molecular sieve exclusion chromatography in combination with multi-angle laser scatterometry. Then, product A is separated by column chromatography to prepare oligosaccharides with single polymerization degree: from disaccharide to decasaccharide. These oligosaccharides with single polymerization degree are compared for biological activity in vitro and in vivo. It has been found that hexasaccharide has the best activity among the 9 oligosaccharides, which is similar to the results of prior patents, e.g., the oligosaccharide activity results disclosed in prior patent application document 1.

The inventors of the present patent application have found that when the above 9 oligosaccharides having novel structures are compounded in a certain ratio, a highly active oligosaccharide composition having a higher activity than the most active hexasaccharide can be obtained. The proportions of various oligosaccharides in the highly active oligosaccharide composition need to be combined according to the following proportional relationship:

The total weight of mannuronic diacid oligosaccharides wherein $n=1-5$ in the composition is 80-95% of the total weight of the composition, and the total weight of mannuronic diacid oligosaccharides wherein $n=1-3$ is 20-70% of the total weight of the composition. The ratio of the total weight of mannuronic diacid oligosaccharides wherein $n=1-3$ to the total weight of mannuronic diacid oligosaccharides wherein $n=4-7$ is between 1.0 and 3.5, preferably between 1.0 and 3.0.

The present invention provides a formula for preparing a highly active oligomannaric acid oligosaccharide composition.

The mannuronic diacid oligosaccharide composition of the present invention can inhibit cell damage and protect nerve cells. In an animal model, the mannuronic diacid oligosaccharide composition provided by the present invention can significantly improve the learning and cognitive functions of dementia model animals. Therefore, the mannuronic diacid oligosaccharide composition provided by the present invention has potential effects of preventing and treating Alzheimer's disease.

In an exemplary embodiment, the method of the present invention includes the following steps:

(1) Preparation of Mannuronic Diacid Product:

Preparation of M-segment intermediate. As described above, the starting material M-segment intermediate used in the present invention can be produced by a method known in the prior art, e.g., the methods disclosed in Chinese Patent Application No. 98806637.8 and CN02823707.2. A common method can be simply described below: alginic acid is preliminarily degraded to give a polysaccharide mixture of polymannuronic acid and polyguluronic acid; the polysaccharide mixture is subjected to acidic precipitation to remove the polyguluronic acid therein; and further refinement is conducted to obtain a homopolymannuronic acid having a purity of 90% or more, i.e., an M-segment intermediate.

Ozone oxidative degradation. The M-segment intermediate is dissolved in an appropriate amount of water and stirred at room temperature or under heating. Ozone is continuously charged to initiate the reaction. The pH of the reaction can be adjusted to 3-13, preferably 4-10, more preferably 6-8 by dropwise adding dilute hydrochloric acid or a dilute NaOH solution. The temperature is preferably 0-70° C., more preferably 10-45° C. After the reaction is completed, the charging of ozone is stopped and the pH is adjusted to neutral.

Membrane separation and purification. The reaction product obtained above is formulated into a solution at a concentration of about 10%, and separated by a molecular cut-off membrane to remove degradation products below monosaccharide, and collect the retentate. The molecular cut-off membrane used has an MWCO of 1000-3000 Da, preferably 2000 Da. The collected liquid is concentrated on a rotary evaporator and dried under vacuum to obtain an oligomannuronic diacid mixture. These products are found to be compositions comprising oligosaccharides, i.e., from disaccharide to decasaccharide, with contents being within certain ranges. Three compositions, A, B and C, were prepared according to the foregoing method. The proportions and structures of oligosaccharides in these compositions were confirmed in Examples 1-3.

(2) Preparation of Oligosaccharides with a Single Polymerization Degree

The oligosaccharide mixture obtained in step (1) is dissolved to a concentration of about 10%, separated on a P6 gel chromatographic column, and subjected to ultraviolet detection to collect each effluent component. The components having the same polymerization degree are combined. Nine components of from disaccharide to decasaccharide are collected, desalted by G10 gel column chromatography, concentrated on a rotary evaporator, and dried under vacuum. The specific purification and preparation processes are shown in Example 4. These operations of column chromatography, desalting and drying are known to those skilled in the art.

The 9 oligosaccharides with single polymerization degree were evaluated for pharmacological activity in an animal model of senile dementia. It was found that hexasaccharide had the best activity. See Example 4 for details.

(3) Comparison of Activities of Oligosaccharide Compositions

The oligosaccharides with single polymerization degree as prepared in the above step (2) are compounded in the mass percentages as shown in the following table to obtain a fourth composition, i.e., composition D. The proportions of oligosaccharides in the three oligosaccharide compositions A, B and C from the above step (1) and composition D are shown in the following table:

| | disaccharide | trisaccharide | tetrasaccharide | pentasaccharide | hexasaccharide | heptasaccharide | octasaccharide | nonasaccharide | decasaccharide |
|---|---|---|---|---|---|---|---|---|---|
| A | 19% | 25% | 22% | 13% | 9% | 6% | 3% | 2% | 1% |
| B | 24% | 25% | 19% | 12% | 9% | 5% | 3% | 2% | 1% |
| C | 8% | 20% | 28% | 19% | 13% | 6% | 3% | 2% | 1% |
| D | 5% | 30% | 20% | 20% | 5% | 5% | 5% | 5% | 5% |

The above four compositions and the hexasaccharide purified in step (2) are compared for pharmacological activities. The results show that the four oligosaccharide compositions A, B, C and D are significantly more active than hexasaccharide that has the best activity in the oligosaccharides with single polymerization degree. It can be seen that a single oligosaccharide can play a synergistic effect after compounding. After compounding, the oligosaccharides that are less active, such as disaccharide and trisaccharide, are more active than hexasaccharide.

In summary, the present invention provides a method for preparing a highly active mannuronic diacid oligosaccharide composition, comprising an oxidative degradation reaction using the M-segment intermediate as a raw material in the presence of ozone, and separation and purification of the reaction product through ultrafiltration membrane. The preparation process involves a simple production process and a high yield, and the reaction product can be easily purified to obtain a product having a good activity. The inventors also reveal ranges of the mass percentages and proportions of various oligosaccharides in the highly active composition. The significance of the preparation process provided by the present invention lies in that a mannuronic diacid having a novel structure, i.e., a diacid residue having 6 possible structures at the reducing end of the sugar chain, is obtained, and that the prepared oligosaccharide composition comprises moderate proportions of various oligosaccharides and has a strong biological activity.

The present invention further provides a medicament or health care product comprising an mannuronic diacid oligosaccharide composition as described above, and optionally a pharmaceutically acceptable carrier or excipient.

Methods for preparing oligosaccharide combination drugs containing active ingredients in various proportions are known, or apparent to those skilled in the art from the disclosure of the present invention, for example, as described in Remington's Pharmaceutical Sciences, Martin, E. W., ed., Mack Publishing Company, 19th ed. (1995). Methods for preparing the pharmaceutical composition comprise incorporation of suitable pharmaceutical excipients, carriers, diluents and the like.

The pharmaceutical preparation of the present invention is prepared by a known method, including conventional mixing, dissolving or lyophilizing.

The pharmaceutical composition of the present invention can be administered to a patient via a variety of routes suitable for the chosen mode of administration, such as orally or parenterally (via intravenous, intramuscular, topical or subcutaneous routes).

Accordingly, the combination drug of the present invention can be administered systemically, for example, orally, in combination with a pharmaceutically acceptable carrier such as an inert diluent or an edible carrier. It may be enclosed in hard or soft shell gelatin capsules, or it may be compressed into tablets. For oral therapeutic administration, the active compound of the present invention may be incorporated with one or more excipients and used in the form of swallowable tablets, buccal tablets, troches, capsules, elixirs, suspensions, syrups, wafers, and the like. Such compositions and preparations should contain at least 0.1% of active compound. The proportion of the compositions and preparations may, of course, be varied and may be in a range of from about 1% to about 99% by weight of a given unit dosage form. The amount of an active compound in such therapeutically useful compositions is such that an effective dosage level can be obtained.

The tablets, troches, pills, capsules and the like may also contain: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, oil of wintergreen, or cherry flavoring. When the unit dosage form is a capsule, it may contain, in addition to materials of the above type, a liquid carrier such as vegetable oil or polyethylene glycol. Various other materials may be presented as coatings or to otherwise modify the physical form of the solid unit dosage unit. For instance, tablets, pills, or capsules may be coated with gelatin, wax, shellac, or sugar. Syrups or elixirs may contain the active compound, sucrose or fructose as a sweetening agent, a methylparaben or propylparaben as a preservative, a dye and flavoring agent such as cherry or orange flavor. Of course, any material used for preparing any unit dosage form should be pharmaceutically acceptable and non-toxic in the amounts employed. In addition, the active compound may be incorporated into sustained-release formulations and sustained-release devices.

The active compound may also be administered intravenously or intraperitoneally by infusion or injection. Solutions of the active compound or a salt thereof can be prepared in water optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders of the active ingredient (optionally encapsulated in liposomes) included in an extemporaneous preparation of a sterile solution or dispersion suitable for injection or infusion. In all cases, the final dosage form must be sterile, liquid, and stable under the conditions of manufacture and storage. The liquid carrier can be a solvent or a liquid dispersion medium comprising, for example, water, ethanol, polyol (e.g., glycerol, propylene glycol, liquid polyethylene glycol, and the like), vegetable oils, non-toxic glyceride, and suitable mixtures thereof. The proper fluidity can be maintained, for example, by formation of liposomes, by the maintenance of the required particle size in the case of dispersion, or by the use of surfactants. The action of anti-microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various other ingredients enumerated above, as required, followed by filtered sterilization. In the case of sterile powders for the preparation of sterile injectable solution, the preferred methods of preparation are vacuum drying and the freeze-drying technique which yield a powder of the active ingredient plus any additional desired ingredient from previously sterile-filtered solution thereof.

Useful solid carriers include pulverized solids (e.g., talc, clay, microcrystalline cellulose, silica, alumina, etc.). Useful liquid carriers include water, ethanol, ethylene glycol or a water-ethanol/ethylene glycol mixture. The combination drug of the present invention may be dissolved or dispersed in the carrier in an effective amount, optionally with the aid of a non-toxic surfactant. Adjuvants (such as fragrances) and additional antimicrobial agents can be added to optimize the properties for a given use.

Thickeners (such as synthetic polymers, fatty acids, fatty acid salts and esters, fatty alcohols, modified celluloses or modified inorganic materials) can also be used with liquid carriers to form coatable pastes, gels, ointments, soap, etc., which can be directly applied to the user's skin.

The therapeutically required amount of the compound or a mixture thereof depends not only on the compound per se, but also on the mode of administration, the nature of the disease to be treated, and the age and condition of the patient, ultimately depending on the decision of the attending physician or clinician.

The above preparations may be present in unit dosage form, which is a physically discrete unit containing a unit dose, and is suitable for administration to human and other mammalian bodies. The unit dosage form can be a capsule or tablet, or a plurality of capsules or tablets. The amount of unit dose of the active ingredient may vary or be adjusted between about 0.1 and about 1000 mg or more, depending on the particular treatment involved.

Animal Model and Steps for Evaluating Efficacy and Activity

1. Animal model for evaluating efficacy against AD: An AD model is induced by unilateral intraventricular injection of Aβ, and learning and memory behaviors of the AD model rats are evaluated by the Morris water maze test.

Male Wistar rats are used, each weighing between 180 and 220 g. Randomization: a sham-operation control group, a model group, and dosing groups, 14 animals per group. The rats are anesthetized by intraperitoneal injection of pentobarbital sodium (40 mg/kg) and fixed on a stereotaxic apparatus. The skin is routinely prepared, sterilized, cut, and the anterior fontanel is exposed. The hippocampal CA1 region is located at a position "3.0 mm after the anterior fontanel, 2.2 mm next to the raphe, and 2.8 mm under the dura mater" as described in the Stereotaxic Map of Rat Brain, Xinming Bao and Siyun Shu, Beijing, People's Medical Publishing House, 1991, 28. For the model group and the dosing groups, 5 μl of aggregated Aβ (A131-40 is formulated in a PBS solution to 1.4 mg/mL, and incubated in an incubator at 37° C. for 5 days to form an aggregated state) is slowly injected into the right hippocampal CA1 region with a micro-injector needle vertical to the skull, in a flow rate of 1 μL/min. After the injection is completed, the needle is left for 5 min, such that Aβ can be sufficiently dispersed. Then, the needle is slowly withdrawn. The surgical incision is sutured and kept warm for recovery. The control group receives the same procedure except that an equal amount of sterile PBS is injected. The corresponding drug is administered 7 days prior to the operation, and the administration is continued until the end of the experiment.

The Morris water maze test is performed on day 11 after the operation.

Place navigation test: Each group of rats is trained once a day for 5 consecutive days, i.e., receives a place navigation test. The time taken by the animals to find the platform (i.e., escape latency) is recorded. The rats that fail to find the platform in about 90 s are guided to swim to the platform in a straight line direction and stand on the platform for 30 s, to induce their learning and memory.

Spatial probe test: On the second day after the end of the place navigation test, the platform is removed, and the rats are placed into water from the place of entry. The number of times the animals pass through the platform and the percentage of the swimming distance in the quadrant where the platform is located relative to the total distance are recorded. The learning and memory functions of the animals are evaluated.

2. Model for evaluating cell viability: SH-SY5Y cells (neuroblastoma cells) are seeded in a 96-well plate (3000 cells/well). After 24 hr, the medium is removed and a drug is added for pretreatment for 0.5 hr (formulated in a serum-free culture medium; 3 replicates per dose). Then, aggregated Aβ1-42 (Aβ1-42 is formulated in a PBS solution to 1 mg/mL, and incubated in an incubator at 4° C. for 24 hr to form an aggregated state, at a final concentration of 2 μM) is added and incubated for 48 hr. The cell viability is detected by CCK8.

Advantages of the present invention are further illustrated in the following non-limiting examples. However, the specific materials and amounts thereof as well as other experimental conditions used in the examples should not be construed as limiting the present invention. The parts, proportions, percentages, and the like in the present invention are all expressed by mass unless otherwise specified.

EXAMPLES

Example 1

Step 1): Preparation of a Mannuronic Diacid Oligosaccharide Mixture

An M-segment intermediate was prepared by the method disclosed in prior patents. The specific operations are simply described below: 5 Kg of sodium alginate was formulated into a ~10% solution, and the pH was adjusted to about 3.0 by adding dilute hydrochloric acid. The solution was heated to 80° C., and stirred. It was allowed to react for 10 hr before the heating was stopped. After cooling to room temperature, the pH was adjusted to 9.0 by adding NaOH, and further adjusted to 2.85 by adding dilute hydrochloric acid. The solution was centrifuged at 5000 rpm for 10 min. The supernatant was collected, and adjusted to pH 1.0 by adding HCl. After centrifugation, the precipitate was collected, concentrated on a rotary evaporator, and dry in vacuo to give 1500 g of the M-segment intermediate. 500 g of the M-segment intermediate was weighed, and dissolved in distilled water to prepare a solution in a volume of 5 L. The solution was adjusted to pH 6.5 with NaOH, and heated in a water bath to control the reaction temperature at 75° C. The gas flow rate at the outlet of an oxygen cylinder and the power of an ozone generator were adjusted such that ozone was fed into the reaction solution at a mass concentration flow rate of 8 g/hr. After 4 hr of reaction, the feeding of ozone was stopped, and a suitable amount of water was added to adjust the concentration of the solution to about 10%. The solution was filtered through an ultrafiltration membrane with a molecular weight cut-off of 2,000 Da to collect a retentate. The collected liquid was concentrated on a rotary evaporator and dried under vacuum to obtain 350 g of mannuronic diacid product A.

Step 2): Analysis of Proportions and Structures of Oligosaccharides with Various Polymerization Degrees in Mannuronic Diacid Product A 100 mg of the above dried mannuronic diacid product A was accurately weighed, dissolved in water to a concentration of 10 mg/mL, and passed through a 0.22 um filter membrane to obtain a test sample solution. The proportions of oligosaccharides with different polymerization degrees in the composition were determined by Superdex peptide molecular exclusion chromatography (GE Co.) in combination with multi-angle laser light scattering (MALS, Wyatt Co.). The experimental conditions were as follows:

Chromatographic column: Superdex peptide 10/300 Gl
Mobile phase: 0.1 mol/L NaCl
Injection volume: 10 μL
Flow rate: 0.3 mL/min Test results: from disaccharide to decasaccharide were represented by dp2-dp10, respectively. dp2 was 19%, dp3 was 25%, dp4 was 22%, dp5 was 13%, dp6 was 9%, dp7 was 6%, dp8 was 3%, dp9 was 2%, and dp10 was 1%.

Step 3): LC-MS Analysis of Structures of Oligosaccharides with Various Polymerization Degrees in Mannuronic Diacid Product A Experimental Conditions:

Chromatographic column: Superdex peptide 10/300 Gl
Mobile phase: 20% methanol+80% 80 mmol/L $NH_4Ac$
Flow rate: 0.1 mL/min
Column temperature: 25±0.8° C.
Mass spectrometry conditions: Agilent 6540 QTOF; ion source: ESI collision voltage 120 V; negative ion mode. The width of acquired signal (m/z) was 100-1000.

Figure 2:
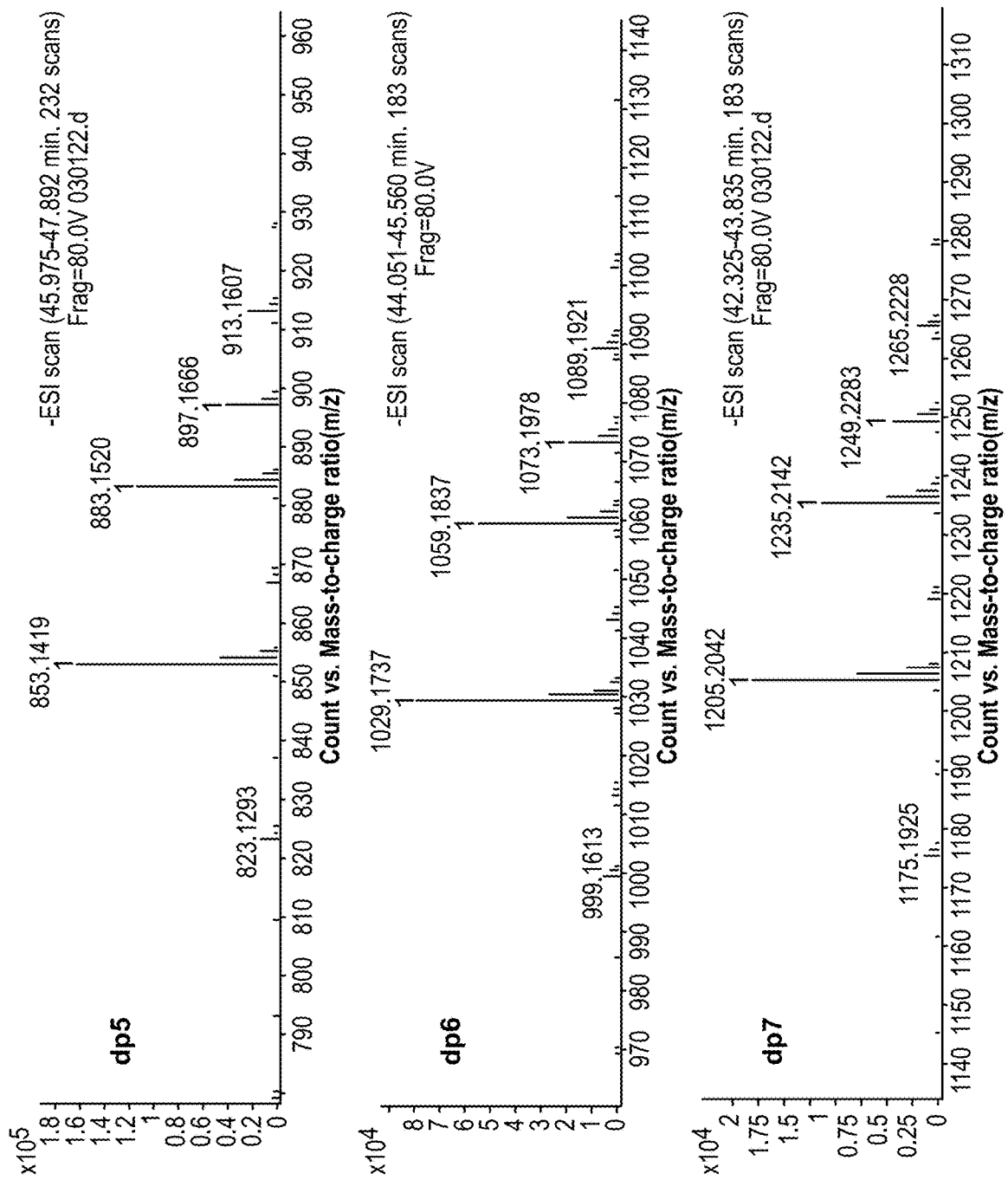
FIG. 2 shows mass spectra of pentasaccharide, hexasaccharide and heptasaccharide in product A.
Figure 3:
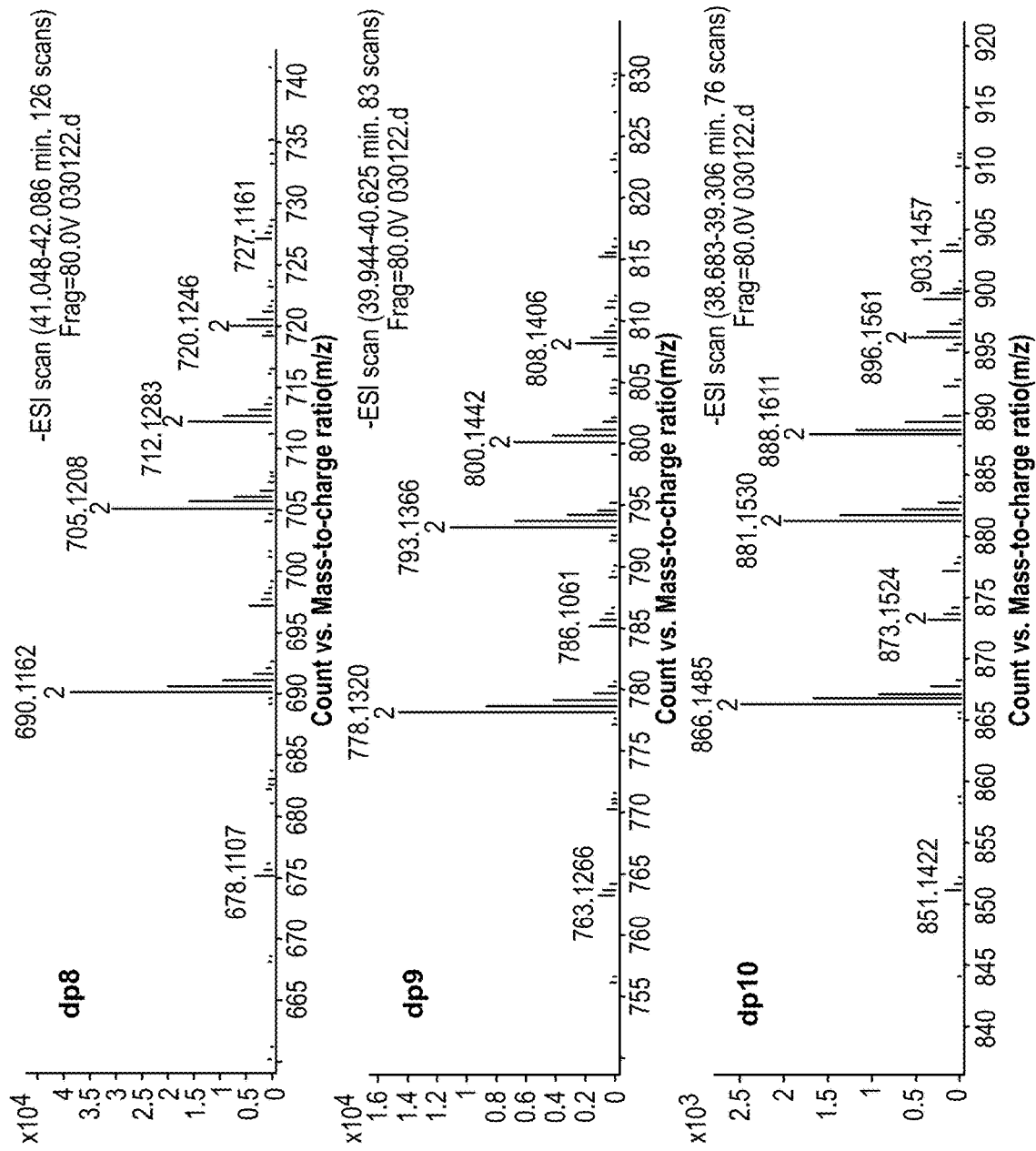
FIG. 3 shows mass spectra of octasaccharide, nonasaccharide and decasaccharide in product A.

The mass spectra of oligosaccharides with various polymerization degrees are shown in FIGS. 1-3. Various signal peaks in the mass spectra were assigned, confirming the molecular structures of all oligosaccharides in product A, i.e., the structure as shown in Formula (III). The signal assignments and the structures corresponding to the signals are shown in Table 1 below.

TABLE 1

6 diacid structures of oligosaccharides with different polymerization degrees in product A and their mass-to-charge ratios in mass spectra

| | | | Mass-to-charge ratio (m/z) | | | | |
| --- | --- | --- | --- | --- | --- | --- | --- |
| No. | Molecular structure | Molecular formula | n = 1 $[M-1]^-$ | n = 2 $[M-1]^-$ | n = 3 $[M-1]^-$ | n = 4 $[M-1]^-$ | n = 5 $[M-1]^-$ |
| 1 | [structure] | $(C_6H_8O_6)_n C_6H_{10}O_8$ N = 1-9 | 385 | 561 | 737 | 913 | 1089 |
| 2 | [structure] | $(C_6H_8O_6)_n C_5H_8O_7$ N = 1-9 | 355 | 531 | 707 | 883 | 1059 |
| 3 | [structure] | $(C_6H_8O_6)_n C_5H_8O_7$ N = 1-9 | 355 | 531 | 707 | 883 | 1059 |
| 4 | [structure] | $(C_6H_8O_6)_n C_4H_6O_6$ N = 1-9 | 325 | 501 | 677 | 853 | 1029 |
| 5 | [structure] | $(C_6H_8O_6)_n C_4H_6O_6$ N = 1-9 | 325 | 501 | 677 | 853 | 1029 |
| 6 | [structure] | $(C_6H_8O_6)_n C_3H_4O_5$ N = 1-9 | 295 | 471 | 647 | 823 | 999 |

TABLE 1-continued 6 diacid structures of oligosaccharides with different polymerization degrees in product A and their mass-to-charge ratios in mass spectra

| No. | Mass-to-charge ratio (m/z) | | | |
|---|---|---|---|---|
| | n = 6 $[M - 1]^-$ | n = 7 $[M - 2]^{2-}$ | n = 8 $[M - 2]^{2-}$ | n = 9 $[M - 2]^{2-}$ |
| 1 | 1265 | 720 | 808 | 896 |
| 2 | 1235 | 705 | 793 | 881 |
| 3 | 1235 | 705 | 793 | 881 |
| 4 | 1205 | 690 | 778 | 866 |
| 5 | 1205 | 690 | 778 | 866 |
| 6 | 1175 | 675 | 763 | 851 |

It was found from the above mass spectrometric structural analysis that the mannuronic acid at the reducing end of the sugar chain in product A was oxidized to a saccharic acid structure (see Formula III), which could be a mannaric acid structure comprising 6 carbon atoms (m+m'=3), with a content of about 10-30%, or a decarboxylation product of mannaric acid, i.e., a saccharic acid comprising 5 carbon atoms (m+m'=2) (30-50%) and a saccharic acid comprising 4 carbon atoms (m+m'=1) (30-40%).

Step 4) Evaluation of Pharmacological Activity

1. Protective Effect of Product A on Aβ-Induced Nerve Cell Injury

The test was conducted according to the "model for evaluating cell viability", and the experimental procedure was as follows: SH-SY5Y cells (neuroblastoma cells) were seeded in a 96-well plate (3000 cells/well). After 24 hr, the medium was removed, and for the dosing groups, 10 μL per well of a drug (10 mg/mL) was added for pretreatment for 0.5 hr (formulated in a serum-free culture medium; 3 replicates per dose). Then, aggregated Aβ 1-42 (Aβ1-42 was formulated in a PBS solution to 1 mg/ml, and incubated in an incubator at 4° C. for 24 hr to form an aggregated state, at a final concentration of 2 μM) was added and incubated for 48 hr. The cell viability was detected by CCK8.

Figure 4:
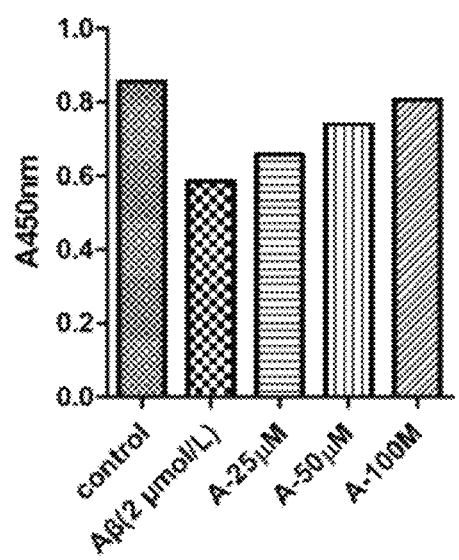
FIG. 4 shows the protective effect of product A at different concentrations on Aβ-induced nerve cell damage.

The results showed that treatment of SH-SY5Y cells with 2 μM Aβ1-42 could induce significant cell damage and decreased cell viability after 48 hours, while 25, 50 and 100 m/mL product A could significantly inhibit Aβ-induced decrease in cell viability; see FIG. 4. The above results indicate that product A can protect nerve cells from the toxic effects of Aβ at a low concentration (25 μg/mL), a medium concentration (50 m/mL), and a high concentration (100 m/mL).

Example 2

100 g of the M-segment intermediate from Example 1 was weighed, and dissolved in distilled water to prepare a solution in a volume of 0.8 L. The solution was adjusted to pH 4.0 with NaOH, and the reaction was carried out at room temperature (25° C.). The gas flow rate at the outlet of an oxygen cylinder and the power of an ozone generator were adjusted such that ozone was fed into the reaction solution at a mass concentration flow rate of 1 g/hr. After 10 hr of reaction, the feeding of ozone was stopped, and a suitable amount of water was added to adjust the concentration of the solution to about 15%. The solution was filtered through an ultrafiltration membrane with a molecular weight cut-off of 1,000 Da to collect a retentate. The collected liquid was concentrated on a rotary evaporator and dried under vacuum to obtain 80 g of mannuronic diacid product B.

The proportions of oligosaccharides with various polymerization degrees in B were determined by Superdex peptide molecular exclusion chromatography (GE Co.) in combination with multi-angle laser light scattering (MALS, Wyatt Co.). The measurement method was the same as that in Example 1. Test results: from disaccharide to decasaccharide were represented by dp2-dp10, respectively. dp2 was 24%, dp3 was 25%, dp4 was 19%, dp5 was 12%, dp6 was 9%, dp7 was 5%, dp8 was 3%, dp9 was 2%, and dp10 was 1%.

Example 3

100 g of the M-segment intermediate of Example 1 was weighed, and dissolved in distilled water to prepare a solution in a volume of 1.5 L. The solution was adjusted to pH 9.0 with NaOH, and the reaction was carried out in a water bath at 45° C. The gas flow rate at the outlet of an oxygen cylinder and the power of an ozone generator were adjusted such that ozone was fed into the reaction solution at a mass concentration flow rate of 3 g/hr. After 2 hr of reaction, the feeding of ozone was stopped, and a suitable amount of water was added to adjust the concentration of the solution to about 5%. The solution was filtered through an ultrafiltration membrane with a molecular weight cut-off of 3,000 Da to collect a retentate. The collected liquid was concentrated on a rotary evaporator and dried under vacuum to obtain 60 g of mannuronic diacid product C.

The proportions of oligosaccharides with various polymerization degrees in C were determined by Superdex peptide molecular exclusion chromatography (GE Co.) in combination with multi-angle laser light scattering (MALS, Wyatt Co.). The measurement method was the same as that in Example 1. Test results: from disaccharide to decasaccharide were represented by dp2-dp10, respectively. dp2 was 8%, dp3 was 20%, dp4 was 28%, dp5 was 19%, dp6 was 13%, dp7 was 6%, dp8 was 3%, dp9 was 2%, and dp10 was 1%.

Example 4

Step 1) Preparation of Mannuronic Diacid Oligosaccharide with Single Polymerization Degree, which was as Follows:

1. Sample Preparation: 300 g of mannuronic diacid product A prepared in Example 1 was dissolved in water to prepare 1000 mL of a concentrated solution, which was placed in a refrigerator at 4° C. for use. For each use, 50 mL of the solution was 1:2 diluted with water, and then suction filtered through a 0.22 um ultrafiltration membrane.
2. Chromatographic separation conditions: The chromatograph was AKTA pure 150 (purchased from GE Co.) equipped with a UV detector and an automatic collector. Separation chromatographic column: 1.2 kg of BioGel P6 (purchased from Bio-Rad Co.) was mixed with deionized water, vacuum degassed, manually filled into a glass column (inner diameter: 10 cm), rinsed with 10 column volumes of pure water. The chromatographic column bed was stable and the height was 1.0 m. Then, the mobile phase was changed to a 0.02 M NaCl solution, and after equilibration with 10 column volumes, sample loading was initiated.
3. Loading and Separation: The flow rate of the pump was set at 1 mL/min. After 100 mL of the sample solution was pumped to the top of the column through the chromatograph's own pump, it was switched to the mobile phase and eluted at a flow rate of 5 mL/min. After outflow of the dead water volume, automatic collection was initiated and 50 mL was collected per tube.
4. The sample loading was repeated, and after 20 repetitions of preparation, the same fractions were combined, concentrated on a rotary evaporator, and lyophilized to obtain a total of 9 oligosaccharides with single polymerization degree from disaccharide to decasaccharide.

Step 2) Evaluation of Pharmacological Activity

The Pharmacological Activities of Oligomannaric Acid Oligosaccharides with Single Polymerization Degree were Evaluated as Follows:

1. Protective Effects of Oligosaccharides on Aβ-Induced Nerve Cell Injury

The experiment was carried out in the same manner as described in Example 1, and the oligosaccharide solutions were prepared at a concentration of 10 mg/mL.

Figure 5:
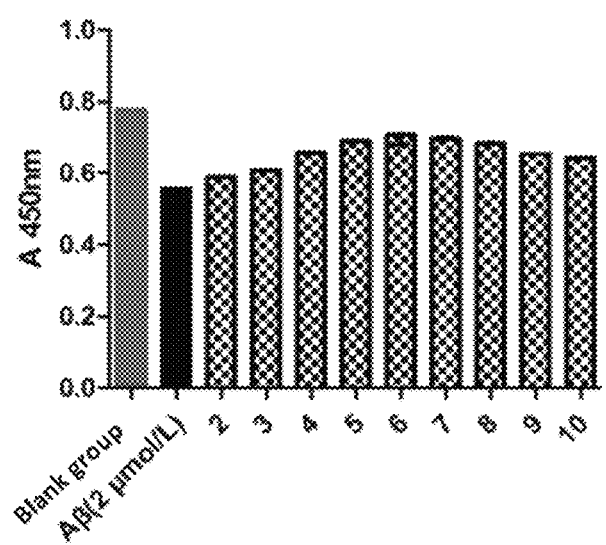
FIG. 5 shows the protective effect of oligomannaric acid with single polymerization degree on Aβ-induced nerve cell damage.

The results showed that treatment of SH-SY5Y cells with 2 μM Aβ1-42 could induce significant cell damage and decreased cell viability after 48 hours, while all the mannuronic diacid oligosaccharides with single polymerization degree had a tendency to inhibit Aβ-induced cell damage. The mannuronic diacid oligosaccharides with a polymerization degree of 4-10 (the final concentration of the drugs was 25 μg/mL) could significantly protect nerve cells from the toxic effects of Aβ, in which the oligosaccharides with four polymerization degrees of 5-8 had better effects, and hexasaccharide had the best activity; see FIG. 5.

2. Effects of Oligosaccharides on the Learning and Memory Impairment Model Induced by Right Intraventricular Injection of Aβ1-40 in Rats The experimental procedure was carried out on 10 g of each of disaccharide to decasaccharide according to the method for "animal model for evaluating efficacy against AD".

Figure 6:
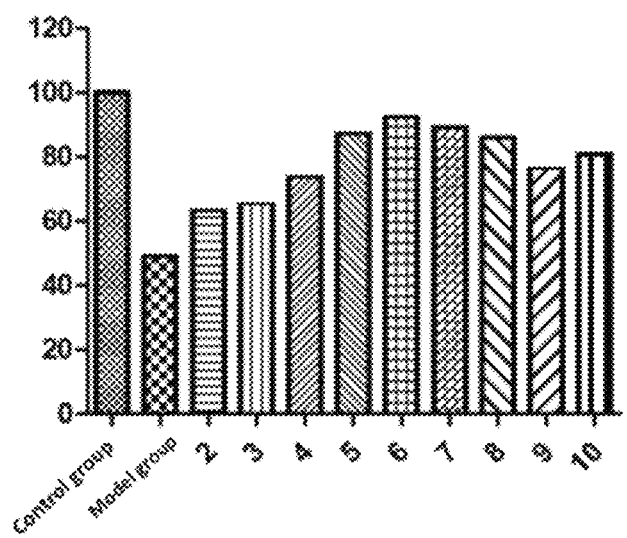
FIG. 6 shows evaluation of the effects of from disaccharide to decasaccharide on an animal model of AD.

Due to the large number of oligosaccharic acids with single polymerization degree, the experiment was completed in multiple batches. The comparison and evaluation of the efficacies of various oligosaccharides was conducted by calculating the percentage of the number of times the animals in each group passed through the platform relative to the number of times the sham-operation control animals passed through the platform. The results showed that the number of passages through the platform was significantly reduced in the model group as compared to the sham-operation control group. Each oligosaccharide with single polymerization degree had a tendency to increase the number of passages through the platform. The mannuronic diacid oligosaccharides with single polymerization degree of 4-10 could significantly increase the number of passages through the platform, in which the oligosaccharides with four polymerization degrees of 5-8 had better effects, and hexasaccharide had the best activity; see FIG. 6.

Example 5

A pharmacological activity evaluation was conducted between the compositions and hexasaccharide to examine the synergistic effect of the oligosaccharides with different polymerization degrees in the compositions and the range of proportions of the oligosaccharides.

Sample Preparation: The mannuronic diacid oligosaccharides with single polymerization degree as prepared in Example 4 were accurately weighed from disaccharide to decasaccharide by the polymerization degree. The weight of each saccharide used was as follows: 0.5 g of disaccharide, 3.0 g of trisaccharide, 2.0 g of tetrasaccharide, 2.0 g of pentasaccharide, 0.5 g of hexasaccharide, 0.5 g of heptasaccharide, 0.5 g of octasaccharide, 0.5 g of nonasaccharide, and 0.5 g of decasaccharide. They were mixed to obtain 10 g of composition product D.

The proportions of oligosaccharides in products A, B, and C prepared in Examples 1, 2, and 3, respectively, and product D prepared in the present Example are shown in Table 2 below.

TABLE 2

Percentages of oligosaccharides in the mannuronic diacid oligosaccharide composition products

| combination | proportion | | | | | | | | |
|---|---|---|---|---|---|---|---|---|---|
| | disaccharide | trisaccharide | tetrasaccharide | pentasaccharide | hexasaccharide | heptasaccharide | octasaccharide | nonasaccharide | decasaccharide |
| A | 19% | 25% | 22% | 13% | 9% | 6% | 3% | 2% | 1% |
| B | 24% | 25% | 19% | 12% | 9% | 5% | 3% | 2% | 1% |
| C | 8% | 20% | 28% | 19% | 13% | 6% | 3% | 2% | 1% |
| D | 5% | 30% | 20% | 20% | 5% | 5% | 5% | 5% | 5% |

10 g of each of the above samples A, B, C, and D was used to compare the pharmacological activities of these compositions and hexasaccharide (6 T) according to the method described in "animal model for evaluating efficacy against AD".

In the experiment, as compared to the sham-operation control group, the animals in the model group had significantly prolonged platform-searching latency, indicating that the evaluation modeling was successful. As compared to the model group, each dosing group had significantly shortened platform-searching latency.

Figure 7:
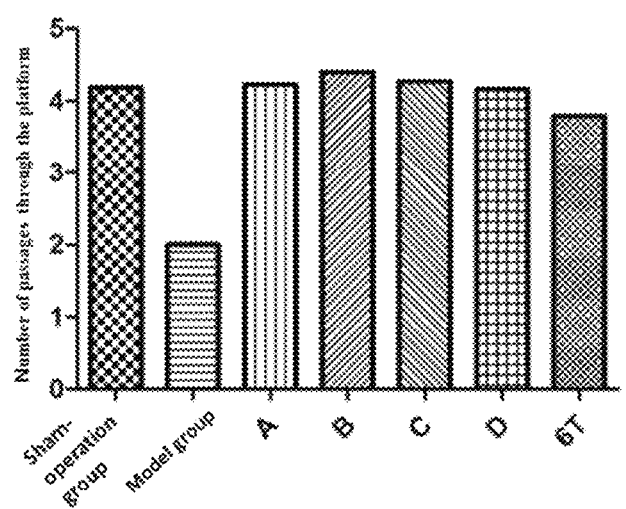
FIG. 7 shows effects of the oligosaccharide compositions and hexasaccharide on the number of times AD animals pass through the platform.
Figure 8:
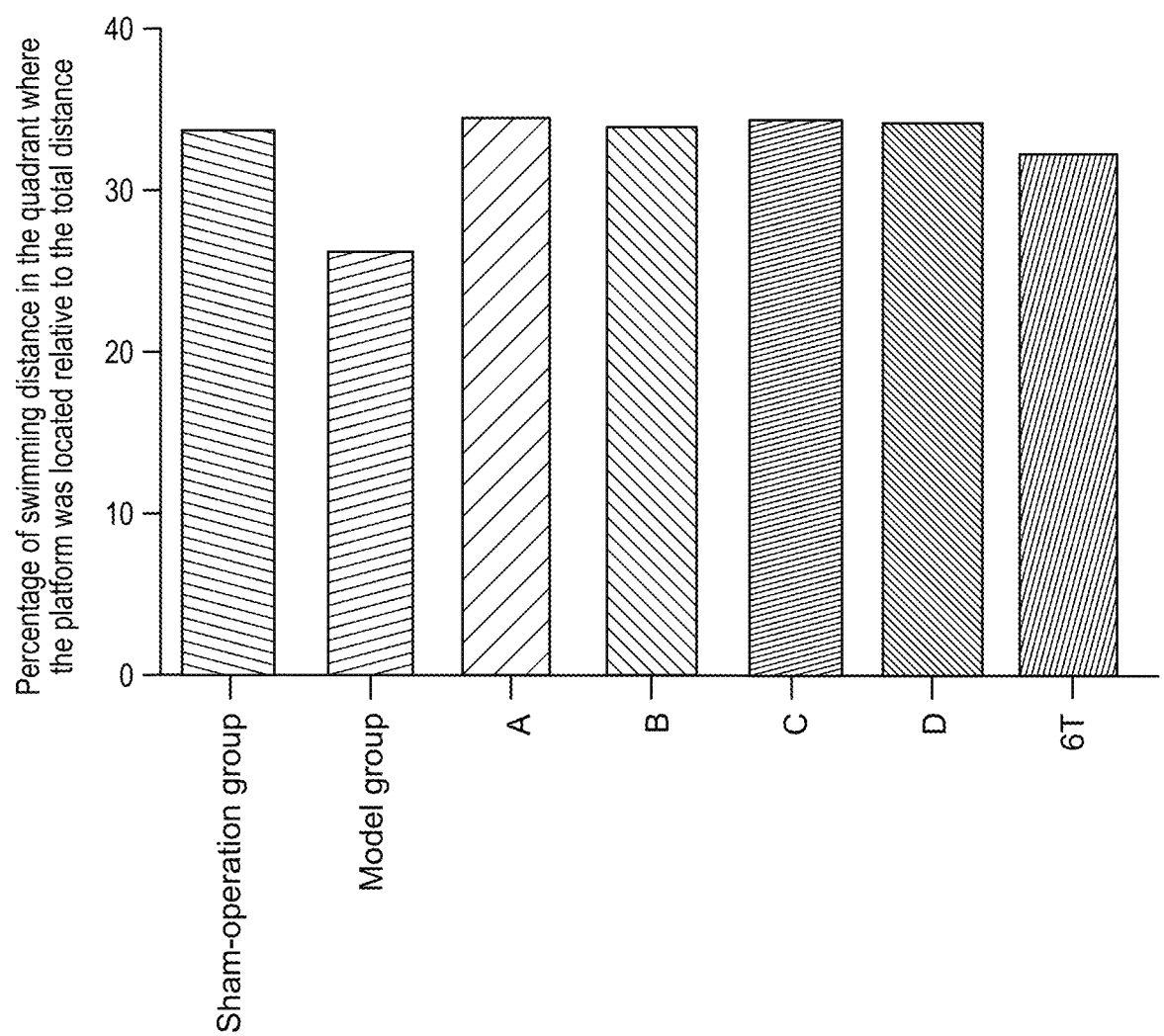
FIG. 8 shows effect of the oligosaccharide compositions and hexasaccharide on swimming distance of AD animals.

There was one resting day after the end of the place navigation training. Then, the platform was removed and a spatial probe test was carried out to observe the number of times animals passed through the platform and the percentage of the swimming distance in the quadrant where the platform was originally located relative to the total distance, and evaluate the memory function of the animals. The results showed that the number of passages through the platform was significantly reduced in the model group and significantly increased in the dosing groups as compared to the sham-operation control group, as shown in FIG. 7. The percentage of the swimming distance in the quadrant where the platform was originally located relative to the total distance showed a similar tendency to the number of passages through the platform. As compared to the sham-operation control group, the percentage of the swimming distance in the quadrant where the platform was originally located relative to the total distance was significantly reduced in the model group, and was significantly increased in the dosing groups, as shown in FIG. 8.

The experimental results showed that the respective pharmacological activities of oligosaccharide compositions A, B, C and D were still very strong on day 4, and stronger than the activity of hexasaccharide with a single polymerization degree, suggesting a synergy between the oligosaccharides in the compositions.

Example 6

A cell co-culturing technique was used to further evaluate the activities of various oligosaccharides with single polymerization degree and the compositions.

Suitable amounts of the oligosaccharides with single polymerization degree as prepared in Example 4 and the oligosaccharide composition product A prepared in Example 1 were accurately weighed, and dissolved in PBS to prepare test drug solutions at a concentration of 10 mg/mL.

The cell co-culturing experiment was substantially the same as the cell culturing method in foregoing Example 1 and Example 4. The main difference lies in that the cell co-culturing technique mimics the interaction of different cells in vivo. Considering that in vivo cells might interact with each other through a signaling pathway, in order to be closer to the in vivo environment, and simulate the interaction between different cells during development of AD, microglial cells were introduced during the culture. The specific experimental procedure was as follows: SH-SY5Y cells (neuroblastoma cells) were seeded in a 24-well plate (12,000 cells/well), and BV-2 cells (microglial cells) were seeded into the upper chamber at a concentration of 15,000 cells/well. After 24 hr, the medium was removed, and the test drug solutions were added to the lower chamber to obtain a final drug concentration of 25 μg/mL. After 0.5 hr of treatment (formulated in a serum-free culture medium; 3 replicates per drug solution), aggregated A131-42 (A01-42 was formulated in a PBS solution to 1 mg/mL, and incubated in an incubator at 4° C. for 24 hr to form an aggregated state, at a final concentration of 2 μM) was added and incubated for 48 hr. The viability of SH-SY5Y cells in the lower chamber was detected by CCK8.

Figure 9:
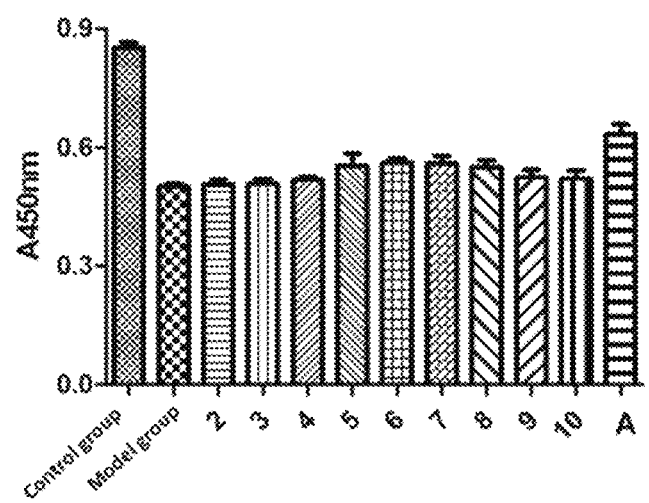
FIG. 9 shows the activities of from disaccharide to decasaccharide and composition A on a cell co-culture model.

After 48 hours, the model group was compared with the normal control group. The former exhibited significant damage and reduced cell survival rate. The dosing groups showed the effect of inhibiting Aβ-induced cell damage. In particular, the activity of product A was significantly better than the activities of other 9 oligosaccharides with single polymerization degree, as shown in FIG. 9. The co-cultured cell model can identify the difference in activity between the composition and the oligosaccharides with single polymerization degree, possibly because a synergistic effect can occur between cytokines released from the microglial cells and the oligosaccharides with different polymerization degrees in the composition, thereby increasing the activity of the oligosaccharide composition.

What is claimed is:

1. A mannuronic diacid saccharide composition, comprising a mixture of mannuronic diacid of Formula (III) or a pharmaceutically acceptable salt thereof:

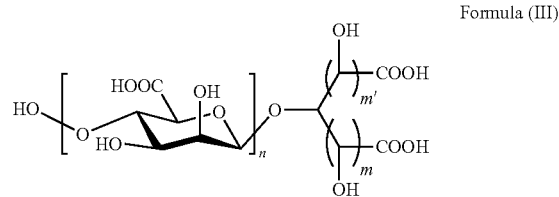

Formula (III)

wherein n is an integer from 1 to 9, m is 0, 1 or 2, and m' is 0 or 1, and wherein, the total weight of mannuronic diacids wherein n=1-5 is 80-95% of the total weight of the composition; and the ratio of the total weight of mannuronic diacids wherein n=1-3 to the total weight of mannuronic diacids wherein n=4-7 is between 1.0 and 3.5; and the total weight of mannuronic diacids wherein m+m'=1 and 2 is equal to or greater than 50% of the total weight of the composition.

2. The mannuronic diacid saccharide composition according to claim 1, wherein the total weight of mannuronic diacids wherein m+m'=1 and 2 is 60-90% of the total weight of the composition.

3. The mannuronic diacid saccharide composition according to claim 1, wherein the total weight of mannuronic diacids wherein m+m'=1 is not less than 10% of the total weight of the composition.

4. The mannuronic diacid saccharide composition according to claim 1, wherein the total weight of mannuronic diacids wherein m+m'=2 is not less than 10% of the total weight of the composition.

5. The mannuronic diacid saccharide composition according to claim 1, wherein the total weight of the mannuronic diacids wherein n=1-3 is 20-70% of the total weight of the composition.

6. The mannuronic diacid saccharide composition according to claim 1, wherein the ratio of the total weight of the mannuronic diacids wherein n=1-3 to the total weight of the mannuronic diacids wherein n=4-7 is between 1.0 and 3.0.

7. The mannuronic diacid saccharide composition of claim 1, wherein the weight percentages of mannuronic diacids with different polymerization degrees in the composition are: 5-25% n=1, 15-30% n=2, 15-25% n=3, 10-25% n=4, 5-15% n=5, 3-10% n=6, 2-5% n=7, 1-5% n=8, and 1-5% n=9.

8. The mannuronic diacid saccharide composition according to claim 7, wherein the weight percentages of mannuronic diacids with different polymerization degrees in the composition are: 10-20% n=1, 18-30% n=2, 15-25% n=3, 15-20% n=4, 5-10% n=5, 3-5% n=6, 2-3% n=7, 1-3% n=8, and 1-3% n=9.

9. The mannuronic diacid saccharide composition of claim 1, wherein the pharmaceutically acceptable salt is a sodium salt or a potassium salt.

10. A pharmaceutical composition or health care product, comprising an effective amount of the mannuronic diacid saccharide composition of claim 1, and, optionally, a suitable carrier.

11. A method for treating a patient with senile dementia, comprising administering an effective amount of the mannuronic diacid saccharide composition of claim 1 to a patient in need thereof.

12. A method for preparing a mannuronic diacid saccharide composition as defined in claim 1, the method comprising ozone oxidative degradation of a homopolymannuronic acid.

13. The method for preparing a mannuronic diacid saccharide composition thereof by ozone oxidative degradation according to claim 12, wherein:
    the oxidation reaction is carried out at a temperature of 0-70° C.; and
    the oxidative degradation step is carried out at a pH of 3-13.

14. The method for preparing a mannuronic diacid saccharide composition according to claim 12, wherein:
    the oxidation reaction is carried out at a temperature of 10-45° C.; and
    the oxidative degradation step is carried out at a pH of 4-10.

15. The mannuronic diacid saccharide composition according to claim 1, wherein the total weight of mannuronic diacids wherein $m+m'=1$ and 2 is 70-90% of the total weight of the composition.

16. The mannuronic diacid saccharide composition according to claim 1, wherein the total weight of mannuronic diacids wherein $m+m'=1$ is 30-40% of the total weight of the composition.

17. The mannuronic diacid saccharide composition according to claim 1, wherein the total weight of mannuronic diacids wherein $m+m'=2$ is 30-50% of the total weight of the composition.

* * * * *